(12) United States Patent
Shuman

(10) Patent No.: US 12,226,598 B2
(45) Date of Patent: Feb. 18, 2025

(54) GUIDE WIRE INTRODUCER

(71) Applicant: GYRUS ACMI, INC., Southborough, MA (US)

(72) Inventor: Brandon J. Shuman, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 618 days.

(21) Appl. No.: 17/190,001

(22) Filed: Mar. 2, 2021

(65) Prior Publication Data
US 2021/0268242 A1  Sep. 2, 2021

Related U.S. Application Data

(60) Provisional application No. 62/984,127, filed on Mar. 2, 2020.

(51) Int. Cl.
*A61M 25/09* (2006.01)
*A61B 17/34* (2006.01)

(52) U.S. Cl.
CPC ....... *A61M 25/09041* (2013.01); *A61B 17/34* (2013.01); *A61M 2025/09116* (2013.01)

(58) Field of Classification Search
CPC .. A61M 25/09041; A61M 2025/09116; A61M 25/0097; A61M 25/0111; A61M 25/01; A61M 25/0102; A61M 2025/0004; A61M 2025/0175; A61M 2025/0063; A61B 17/3439; A61B 2017/00991; A61B 2017/00469; B25G 1/04
See application file for complete search history.

(56) References Cited

U.S. PATENT DOCUMENTS

| | | | | |
|---|---|---|---|---|
| 3,537,451 | A * | 11/1970 | Beck ................. | A61M 25/0111 604/165.03 |
| 5,137,288 | A * | 8/1992 | Starkey ................. | A61M 25/09 279/42 |
| 11,020,564 | B2 * | 6/2021 | Madlung ............ | A61M 25/0111 |
| 2008/0281228 | A1 * | 11/2008 | Parodi ................... | A61M 25/09 600/585 |
| 2012/0123392 | A1 * | 5/2012 | McKinnon ............ | A61M 39/10 604/533 |

(Continued)

FOREIGN PATENT DOCUMENTS

JP   2001321328 A  * 11/2001  ............... A61B 1/00

*Primary Examiner* — Laura A Bouchelle
*Assistant Examiner* — Sarah Dympna Grasmeder
(74) *Attorney, Agent, or Firm* — Schwegman Lundberg & Woessner, P.A.

(57) ABSTRACT

An apparatus for assisting in the introduction of a flexible wire into a device having a comparable sized lumen. An exemplary apparatus includes a first portion having a distal end, a proximal end, a slot and a lumen exposed at the distal end, the proximal end and the slot, and a second portion having a distal end, a proximal end, a slot and a lumen exposed at the distal end, the proximal end and the slot of the second portion. The second portion is slidably and rotatably received with the lumen of the first portion. A gripping device is attached at the proximal end of the second portion. The gripping device causes at least a portion of the proximal end of the second portion to have a reduced inner diameter when a gripping force is applied to the gripping device.

13 Claims, 6 Drawing Sheets

(56) References Cited

U.S. PATENT DOCUMENTS

| | | | |
|---|---|---|---|
| 2013/0103001 A1* | 4/2013 | BenMaamer | A61M 25/09 |
| | | | 604/528 |
| 2017/0239444 A1* | 8/2017 | Parker | A61B 5/6852 |
| 2018/0028800 A1* | 2/2018 | Devgon | A61M 39/0247 |
| 2018/0207406 A1* | 7/2018 | Ishida | A61M 25/0631 |

* cited by examiner

GUIDE WIRE INTRODUCER

BACKGROUND

Thin wires, such as guidewires and stylets used in medical devices (e.g., needles), experience high friction when being pushed through a lumen of the medical device. This makes it difficult to insert the thin guidewires. The guidewire tends to buckle unless the user grabs the guidewire very close to the port of the handle of the medical device that receives the guidewire. Thus, this simple task easily becomes tedious and frustrating.

SUMMARY

An exemplary apparatus includes a first portion having a distal end, a proximal end, a slot that extends from the distal end to the proximal end and a lumen exposed at the distal end, the proximal end and the slot, and a second portion having a distal end, a proximal end, a slot that extends from the distal end to the proximal end of the second portion and a lumen exposed at the distal end, the proximal end and the slot of the second portion. The second portion is slidably and rotatably received with the lumen of the first portion. A gripping device is attached at the proximal end of the second portion. The gripping device causes at least a portion of the proximal end of the second portion to have a reduced inner diameter when a gripping force is applied to the gripping device.

In one aspect, an attachment device rotatably is connected to the distal end of the first portion. The attachment device is configured to attached to a port on a medical device handle. The attachment device includes a proximal end, a distal end and a slot that extends from the proximal end to the distal end of the attachment device.

In another aspect, the gripping device includes a first tab having a first side attached to a first side of the slot at the proximal end of the second portion, and a second tab having a first side attached to a second side of the slot at the proximal end of the second portion.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
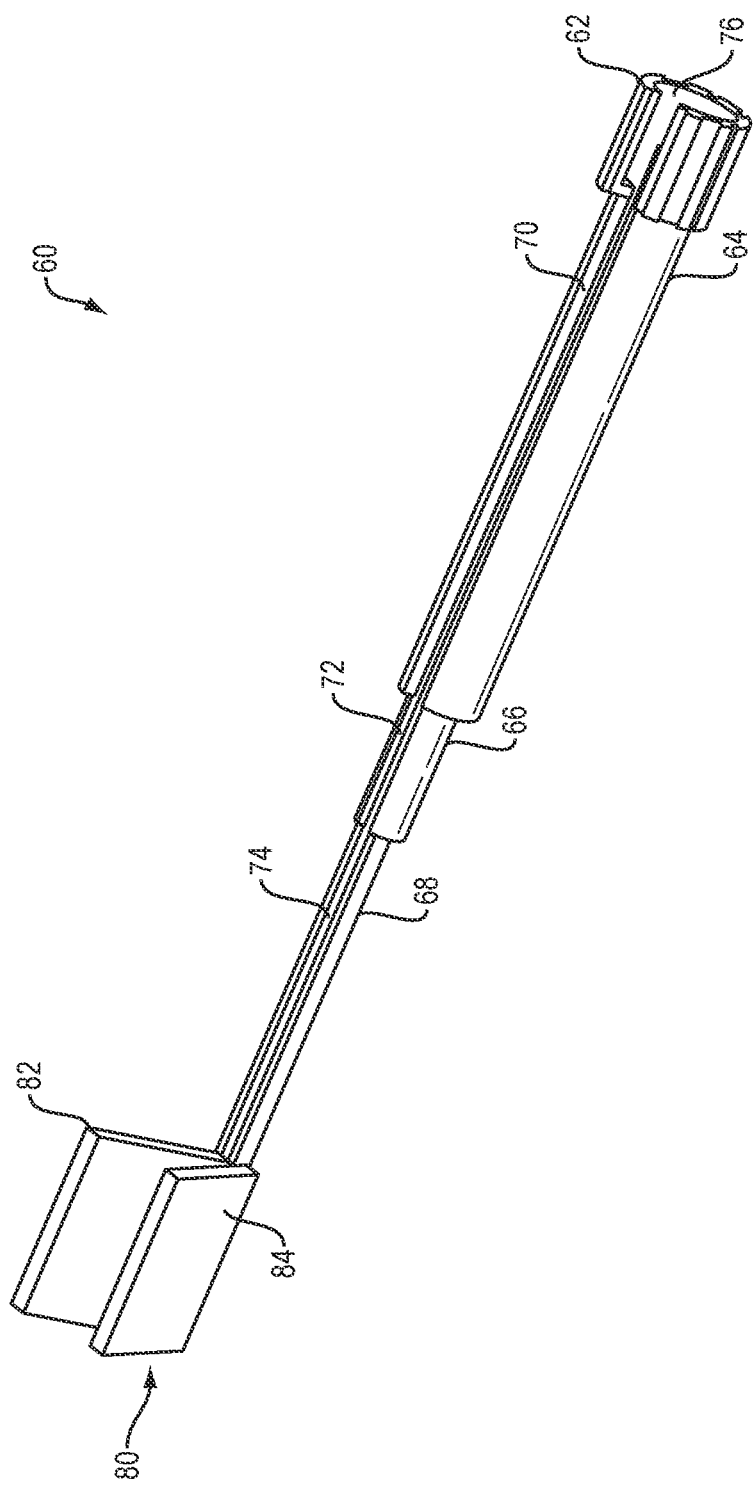
FIG. 1 is a perspective view of an exemplary introducer device.
Figure 2:
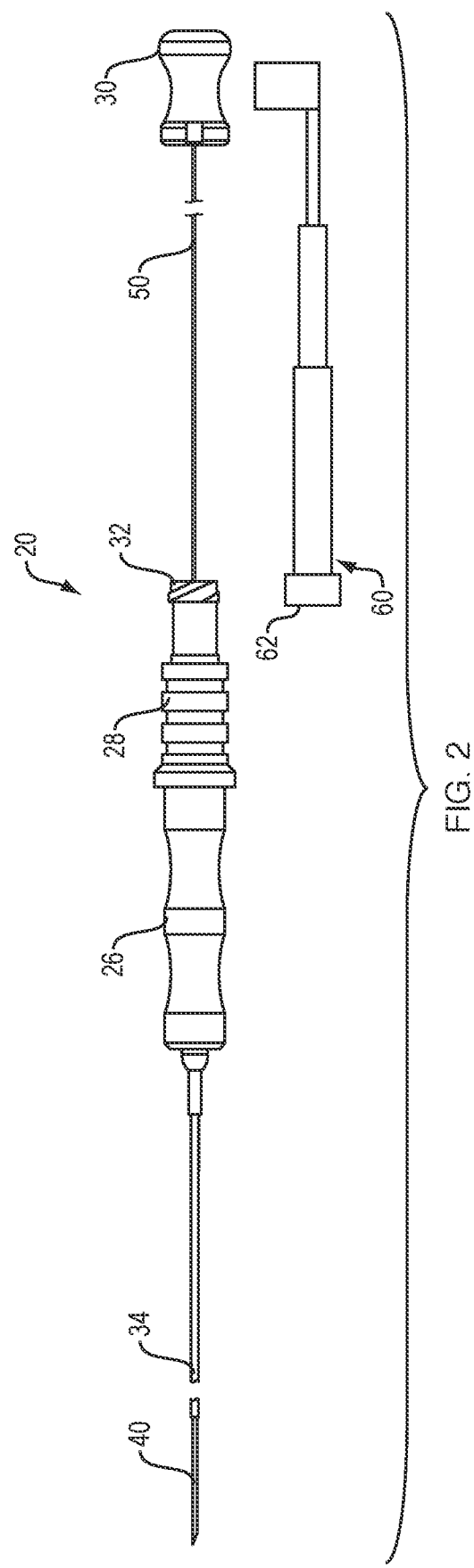
FIG. 2 illustrates a side view of the introducer device of FIG. 1 and a handle of a medical device.

FIG. 1 illustrates an example introducer device 60 for assisting in the advancement of a guidewire/stylet into a lumen of a medical device via a handle component (FIG. 2). The introducer device 60 includes an attachment device 62, a first tube 64, a second tube 66, a third tube 68 and a grasping mechanism 80. Two or more tubes may be used. The attachment device 62 is rotatably attached at a distal end of the first tube 64. The attachment device 62 is designed to attach to a port of a medical device handle. An example of a type of port would include one that includes a feature for the attachment device 62 to attach to, such as a Luer fitting.

The tubes 64, 66, 68 are telescoping tubes with the third tube 68 having the smallest inner diameter and the first tube 64 having the largest inner diameter. The tubes 64, 66, 68 are able to rotate about a longitudinal axis within each other. Each of the tubes 64, 66, 68 includes a slot 70, 72, 74 that extends from their proximal ends to their distal ends. Thus, the tubes 64, 66, 68 do not completely enclosed their lumens. The attachment device 62 also includes a slot 76 that extends from a proximal end to a distal end of the attachment device 62. In a guidewire loading or removing configuration, an operator lines up all the slots 70-76 to allow a guidewire or stylet to slide into or out of the lumens of the tubes 64, 66, 68 and the attachment device 62.

Attached to a proximal end of the third tube 68 is a gripper device 80 that includes two gripper flaps 82, 84. One edge of each of the flaps 82, 84 is attached at or near the slot 74. When an operator squeezes the gripper flaps 82, 84 together, the gripper flaps 82, 84 cause the walls of the proximal end of the third tube 68 to partially collapse. The collapsed condition of the third tube 68 applies a gripping force to a received guidewire/stylet. When not in the collapsed condition, the guidewire/stylet slides within the third tube 68 with minimal friction.

FIG. 2 illustrates the introducer device 60 and an example medical device 20 that the introducer device 60 may attach to. In this example the medical device 20 is a needle aspiration device (e.g., transbronchial needle aspiration (TBNA) device). The medical device 20 includes a handle body 26, a needle actuator 28, a stylet knob 30 and a Luer component 32. The handle body 26 is attached to a proximal end of a sheath 34. The needle actuator 28 includes a shaft portion coupled to a handle portion. The needle actuator 28 receives and is attached to a proximal end of a needle 40. The stylet knob 30 is attached to a proximal end of a stylet 50. The Luer component 32 provides access to a lumen of the needle actuator 28 (shaft and handle portions). The lumen of the needle actuator 28 is aligned with a lumen of the attached needle 40.

Figure 3:
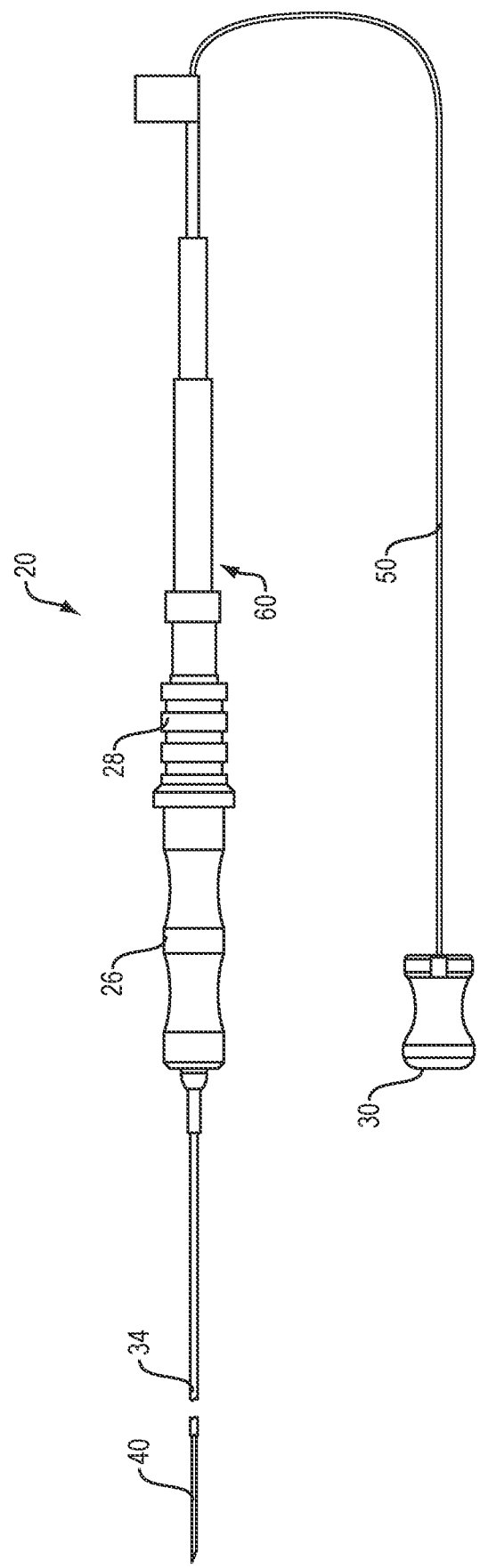
FIG. 3 illustrates the components of FIG. 2 in a first state of operation.
Figure 4:
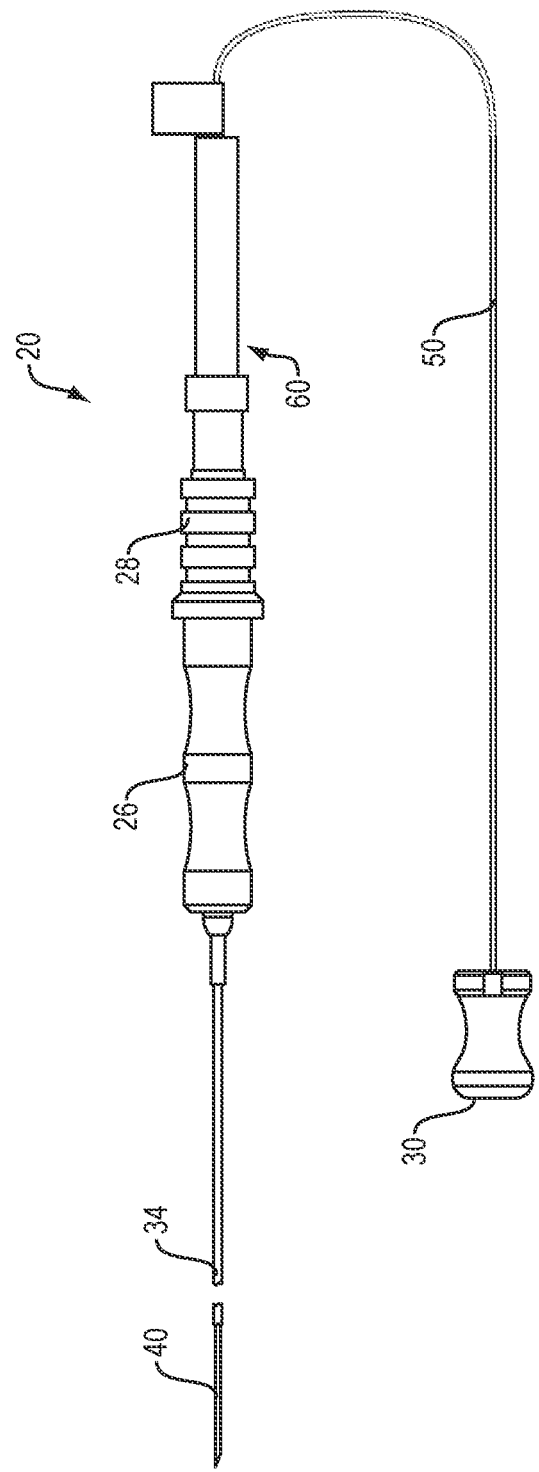
FIG. 4 illustrates the components of FIG. 2 in a second state of operation.

As shown in FIGS. 2 and 3, first, the operator aligns the slots 70-76 then moves the tubes 64, 66, 68 to enclose the stylet 50, preferably in the collapsed position (FIG. 4). In other words, the stylet 50 is inserted into the lumens of the tubes 64, 66, 68 via the slots 70-76. Then, the attachment device 62 is connected to the port of the medical device 20, such as by the Luer component 32. After the attachment device 62 is connected, the tubes 64, 66, 68 are twisted/ rotated in order to remove the slots 70-76 from alignment. This causes the stylet 50 to be captured within the lumens of the tubes 64, 66, 68.

As shown in FIG. 4, the operator then grabs the stylet 50 with the tubes 64, 66, 68, fully or near fully extended, by squeezing the gripper flaps 82, 84 and at least partially sliding the second tube 66 into the third tube 68 then both into the first tube 64. This pushes the stylet 50 into the first tube 64, the handle of the medical device 20 and eventually the lumen of the needle 40.

Figure 5:
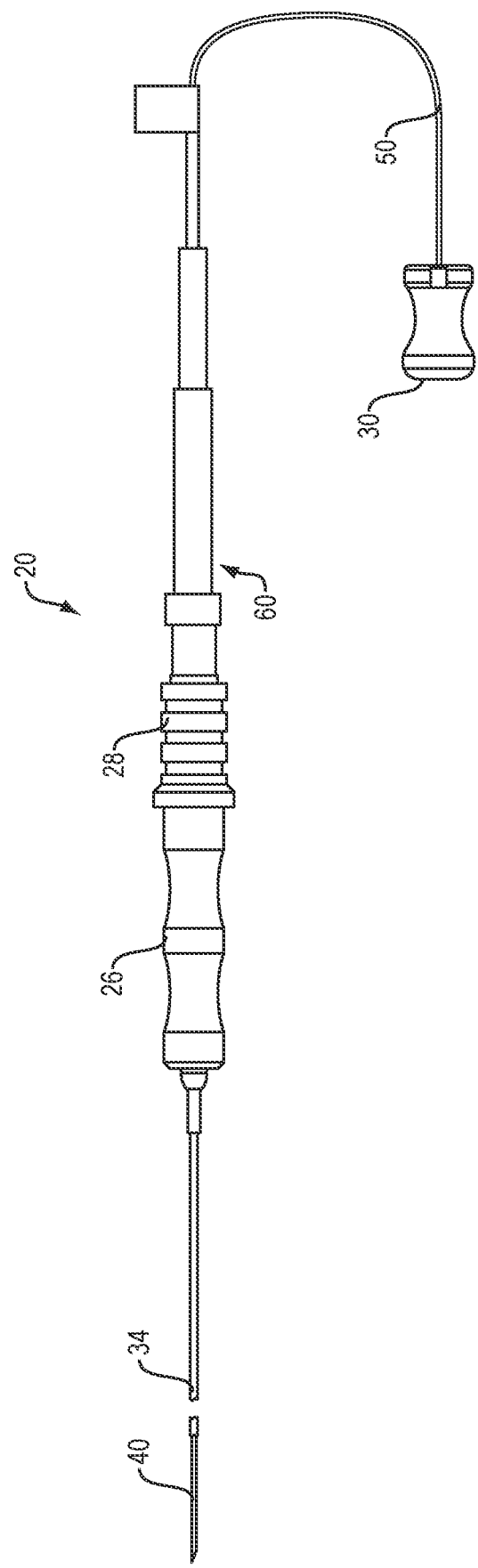
FIG. 5 illustrates the components of FIG. 2 in a third state of operation.

As shown in FIG. 5, the operator releases the squeezing force on the gripper flaps 82, 84 then extends the tubes 66, 68 without moving the stylet 50 from its current position relative to the medical device 20. The steps are then repeated as desired.

Once the operator has inserted the stylet 50 to a point where the stylet knob 30 is at or near the proximal end of the third tube 68, whether telescoped or extended, the operator detaches the attachment device 62 and aligns the slot 76 of the attachment device 62 with the other slots 70, 72, 74. The introducer device 60 can now be removed by allowing the stylet 50 to escape the lumens of the tubes 64, 66, 68 via all the slots 70, 72, 74, 76.

Figure 6:
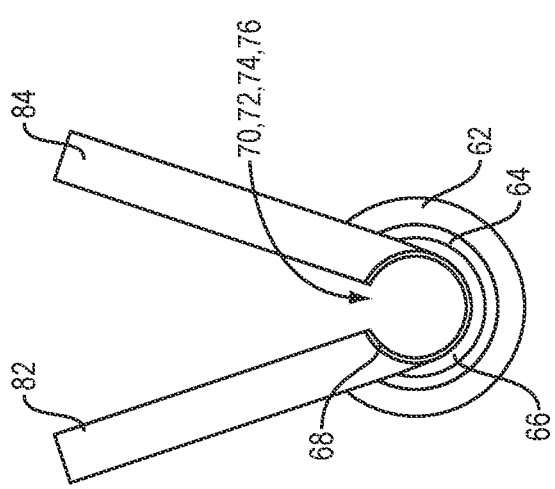
FIG. 6 illustrates an end view of the introducer device of FIG. 1 in a guide wire loading configuration.

FIG. 6 is a proximal end view of the introducer device 60 in a loading configuration (FIGS. 1 and 2). In the loading configuration all the slots 70-76 are approximately co-radial, thus allowing for reception of a guidewire/stylet.

Figure 7:
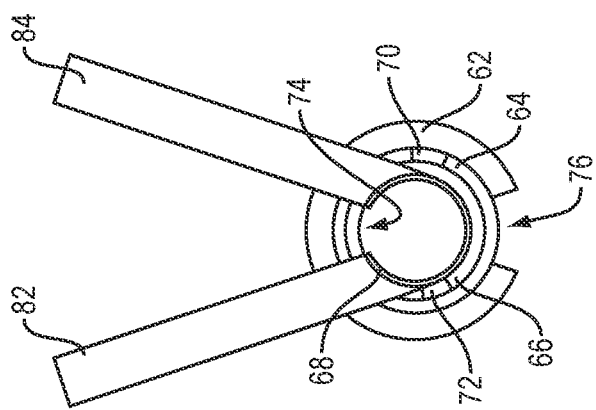
FIG. 7 illustrates an end view of the introducer device of FIG. 1 in a guide wire loaded configuration.

As shown in FIG. 7, the attachment device 62 and the first and second tubes 64, 66 have been rotated so that their slots 70, 72, 76 are no longer aligned with the slot 74 of the third tube 68. This is considered the loaded configuration.

Figure 8:
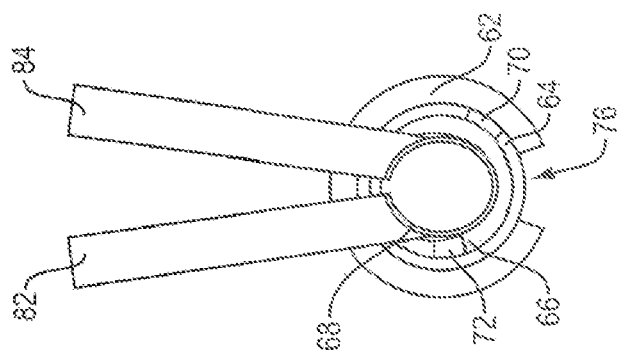
FIG. 8 illustrates an end view of the introducer device of FIG. 1 in a guide wire inserting configuration.

As shown in FIG. 8, the gripper flaps 82, 84 are pinched towards each other by the operator. This pinching action reduces the inner diameter of the third tube 68, thus grabbing the guidewire while the operator at least partially collapses the second and third tubes 66, 68 into the first tube 64 (FIG. 4).

In one embodiment, the static tube may be fairly thin walled.

Also, the tubes 64, 66, 68 may not need to be cylindrical as shown, and a non cylindrical profile may have the advantage of keying the two parts together.

Embodiments

A. An apparatus comprising: a first portion having a distal end, a proximal end, a slot that extends from the distal end to the proximal end and a lumen exposed at the distal end, the proximal end and the slot; a second portion having a distal end, a proximal end, a slot that extends from the distal end to the proximal end of the second portion and a lumen exposed at the distal end, the proximal end and the slot of the second portion, wherein the second portion is configured to be slidably and rotatably received with the lumen of the first portion; and a gripping device attached at the proximal end of the second portion, wherein the gripping device is configured to cause at least a portion of the proximal end of the second portion to have a reduced inner diameter when a gripping force is applied to the gripping device.

B. The apparatus of A, further comprising an attachment device rotatably connected to the distal end of the first portion, wherein the attachment device is configured to attached to a port on a medical device handle.

C. The apparatus of A or B, wherein the attachment device comprises a Luer fitting.

D. The apparatus of any of A-C, wherein the attachment device comprises a proximal end, a distal end and a slot that extends from the proximal end to the distal end of the attachment device.

E. The apparatus of any of A-D, wherein the gripping device comprises: a first tab having a first side attached to a first side of the slot at the proximal end of the second portion; and a second tab having a first side attached to a second side of the slot at the proximal end of the second portion.

F. A medical device comprising: a handle comprising a lumen and a proximal port in communication with the lumen; a flexible component attached at a proximal end to a distal end of the handle, the flexible component comprises a lumen that is aligned with the lumen of the handle when attached thereto; a flexible stylet configured to be slidably received within the lumens of the handle and the flexible component; an apparatus comprising: a first portion having a distal end, a proximal end, a slot that extends from the distal end to the proximal end and a lumen exposed at the distal end, the proximal end and the slot; a second portion having a distal end, a proximal end, a slot that extends from the distal end to the proximal end of the second portion and a lumen exposed at the distal end, the proximal end and the slot of the second portion, wherein the second portion is configured to be slidably received with the lumen of the first portion; a gripping device attached at the proximal end of the second portion; and an attachment device rotatably connected to a distal end of the first portion, wherein the attachment device is configured to attached to the proximal port on the handle.

G. The medical device of F, wherein the attachment device comprises a Luer fitting.

H. The medical device of F or G, wherein the attachment device comprises a proximal end, a distal end and a slot that extends from the proximal end to the distal end of the attachment device.

I. The medical device of any of G-H, wherein the gripping device comprises: a first tab having a first side attached to a first side of the slot at the proximal end of the second portion; and a second tab having a first side attached to a second side of the slot at the proximal end of the second portion.

J. An apparatus comprising: a first portion having a distal end, a proximal end, a slot that extends from the distal end to the proximal end and a lumen exposed at the distal end, the proximal end and the slot; a second portion having a distal end, a proximal end, a slot that extends from the distal end to the proximal end of the second portion and a lumen exposed at the distal end, the proximal end and the slot of the second portion, wherein the second portion is configured to be slidably and rotatably received with the lumen of the first portion; a third portion having a distal end, a proximal end, a slot that extends from the distal end to the proximal end of the third portion and a lumen exposed at the distal end, the proximal end and the slot of the third portion, wherein the third portion is configured to be slidably and rotably received with the lumen of the second portion; and a gripping device attached at the proximal end of the third portion, wherein the gripping device is configured to cause at least a portion of the proximal end of the third portion to have a reduced inner diameter when a gripping force is applied to the gripping device.

K. The apparatus of J, further comprising: an attachment device rotatably connected to the distal end of the first portion, wherein the attachment device is configured to attached to a port on a medical device handle.

L. The apparatus of J or K, wherein the attachment device comprises a Luer fitting.

M. The apparatus of any of J-L, wherein the attachment device comprises a proximal end, a distal end and a slot that extends from the proximal end to the distal end of the attachment device.

N. The apparatus of any of J-M, wherein the gripping device comprises: a first tab having a first side attached to a first side of the slot at the proximal end of the third portion; and a second tab having a first side attached to a second side of the slot at the proximal end of the third portion.

The description of the invention is merely exemplary in nature and variations that do not depart from the gist of the invention are intended to be within the scope of the invention. Such variations are not to be regarded as a departure from the spirit and scope of the invention.

What is claimed is:

1. An apparatus comprising:
   a set of telescoping tubes forming a lumen extending an entire length of the apparatus, each tube of the set of telescoping tubes including a distal end, a proximal end, a slot that extends from the distal end to the proximal end, and a tube lumen exposed at the distal end, the proximal end and the slot,
   wherein the set of telescoping tubes includes a first tube sized to slidably and rotatably receive each additional tube within the set of telescoping tubes and each additional tube within the set of telescoping tubes is slidably and rotatably received within the tube lumen of an adjacent tube of the set of telescoping tubes;
   wherein the slot in each tube is alignable with slots in other tubes in the set of telescoping tubes to form a continuous slot extending the entire length of the apparatus to enable the apparatus to receive an elongate member into the lumen; and
   a gripping device attached to a proximal tube of the set of telescoping tubes, wherein the gripping device includes a pair of opposing flaps extending radially outward from edges of the slot in the tube lumen of the proximal tube, the pair of opposing flaps configured to cause at least a portion of the tube lumen at the proximal end of the proximal tube to have a reduced inner diameter when a gripping force is applied to the gripping device.

2. The apparatus of claim 1, further comprising:
   an attachment device rotatably connected to the distal end of a distal tube of the set of telescoping tubes, wherein the attachment device is configured to be attached to a port on a medical device handle.

3. The apparatus of claim 2, wherein the attachment device comprises a Luer fitting.

4. The apparatus of claim 2, wherein the attachment device comprises a proximal end, a distal end and a slot that extends from the proximal end of the attachment device to the distal end of the attachment device.

5. A medical device comprising:
   a handle comprising a lumen and a proximal port in communication with the lumen;
   a flexible component attached at a proximal end to a distal end of the handle, the flexible component comprises a lumen that is aligned with the lumen of the handle when attached thereto;
   a flexible stylet configured to be slidably received within the lumens of the handle and the flexible component;
   an apparatus comprising:
   a first tube having a distal end, a proximal end, a slot that extends from the distal end of the first tube to the proximal end of the first tube and a lumen exposed at the distal end of the first tube, the proximal end of the first tube and through the slot along an entire length of the first tube;
   a second tube having a distal end, a proximal end, a slot that extends from the distal end of the second tube to the proximal end of the second tube and a lumen exposed at the distal end of the second tube, the proximal end of the second tube and through the slot along an entire length of the second tube, wherein the second tube is configured to be slidably received with the lumen of the first tube;
   a pair of gripper flaps attached at the proximal end of the second tube; and
   an attachment device rotatably connected to the distal end of the first tube, wherein the attachment device is configured to attach to the proximal port on the handle, and wherein the attachment device extends the slot of the first tube.

6. The medical device of claim 5, wherein the attachment device comprises a Luer fitting.

7. The medical device of claim 5, wherein the attachment device comprises a proximal end, a distal end and a slot that extends from the proximal end of the attachment device to the distal end of the attachment device and extends the slot of the first tube.

8. The medical device of claim 5, wherein the pair of gripper flaps comprises:
   a first gripper flap having a first side attached to a first side of the slot at the proximal end of the second tube; and
   a second gripper flap having a first side attached to a second side of the slot at the proximal end of the second tube.

9. An apparatus comprising:
   a first tube having a distal end, a proximal end, a slot that extends from the distal end of the first tube to the proximal end of the first tube and a lumen exposed at the distal end of the first tube, the proximal end of the first tube and through the slot along an entire length of the first tube;
   a second tube having a distal end, a proximal end, a slot that extends from the distal end of the second tube to the proximal end of the second tube and a lumen exposed at the distal end of the second tube, the proximal end of the second tube and through the slot along an entire length of the second tube, wherein the second tube is configured to be slidably and rotatably received with the lumen of the first tube;
   a third tube having a distal end, a proximal end, a slot that extends from the distal end of the third tube to the proximal end of the third tube and a lumen exposed at the distal end of the third tube, the proximal end of the third tube and through the slot along an entire length of the third tube, wherein the third tube is configured to be slidably and rotatably received with the lumen of the second tube; and
   a gripping device attached at the proximal end of the third tube, wherein the gripping device is configured to cause at least a portion of the proximal end of the third tube to have a reduced inner diameter when a gripping force is applied to the gripping device.

10. The apparatus of claim 9, further comprising:
    an attachment device rotatably connected to the distal end of the first tube, wherein the attachment device is configured to be attached to a port on a medical device handle.

11. The apparatus of claim 10, wherein the attachment device comprises a Luer fitting.

12. The apparatus of claim 10, wherein the attachment device comprises a proximal end, a distal end and a slot that extends from the proximal end of the attachment device to the distal end of the attachment device and extends the slot of the first tube.

13. The apparatus of claim 9, wherein the gripping device comprises:
 a first tab having a first side attached to a first side of the slot at the proximal end of the third tube; and
 a second tab having a first side attached to a second side of the slot at the proximal end of the third tube.

* * * * *